US012318480B2

(12) United States Patent
Furukoshi et al.

(10) Patent No.: US 12,318,480 B2
(45) Date of Patent: Jun. 3, 2025

(54) ORAL POUCH PRODUCT

(71) Applicant: JAPAN TOBACCO INC., Tokyo (JP)

(72) Inventors: Masashi Furukoshi, Tokyo (JP);
Atsushi Kuwahara, Tokyo (JP);
Sosuke Watase, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 18/478,524

(22) Filed: Sep. 29, 2023

(65) Prior Publication Data
US 2024/0024230 A1    Jan. 25, 2024

Related U.S. Application Data

(63) Continuation of application No. PCT/JP2022/015843, filed on Mar. 30, 2022.

(30) Foreign Application Priority Data

Mar. 30, 2021 (JP) ................................ 2021-058556

(51) Int. Cl.
A24B 13/00  (2006.01)
A61K 9/00   (2006.01)
A61K 9/14   (2006.01)
A61K 31/465 (2006.01)
A61P 25/34  (2006.01)

(52) U.S. Cl.
CPC ............ *A61K 9/009* (2013.01); *A61K 9/0056* (2013.01); *A61K 9/146* (2013.01); *A61K 31/465* (2013.01); *A61P 25/34* (2018.01)

(58) Field of Classification Search
CPC .......... A24B 3/14; A24B 13/00; A24B 15/243
See application file for complete search history.

(56) References Cited

U.S. PATENT DOCUMENTS

| | | |
|---|---|---|
| 2008/0173317 A1 | 7/2008 | Robinson et al. |
| 2009/0293895 A1 | 12/2009 | Axelsson et al. |
| 2013/0152953 A1 | 6/2013 | Mua et al. |
| 2018/0257801 A1 | 9/2018 | Persson |
| 2020/0138089 A1 | 5/2020 | Duignan et al. |
| 2021/0169132 A1* | 6/2021 | Holton, Jr. ........... A24B 15/243 |

FOREIGN PATENT DOCUMENTS

| | | | |
|---|---|---|---|
| CN | 109419031 A | 3/2019 | |
| JP | 2009-529342 A | 8/2009 | |
| JP | 2016-522680 A | 8/2016 | |
| JP | 2016-536982 A | 12/2016 | |
| JP | 2019-507061 A | 3/2019 | |
| WO | WO-2015057603 A1 * | 4/2015 | .............. A23G 3/48 |
| WO | WO 2020/244721 A1 | 12/2020 | |

OTHER PUBLICATIONS

International Search Report for PCT/JP2022/015843 (PCT/ISA/210) mailed on Jun. 14, 2022.
Japanese Office Action for Japanese Application No. 2023-511464, dated Jan. 7, 2025, with an English translation.
Supplementary European Search Report for corresponding European Application No. 22781053.8; dated Mar. 10, 2025.

* cited by examiner

*Primary Examiner* — Micah Paul Young
(74) *Attorney, Agent, or Firm* — Birch, Stewart, Kolasch & Birch, LLP

(57) ABSTRACT

The present invention addresses the problem of providing an oral pouch product containing a novel oral composition to which a cool feeling (also referred to as sense of coolness, fresh taste, or the like) is imparted. The problem is solved by an oral pouch product formed from an oral composition containing nicotine, a sugar alcohol, and a cool feeling fragrance and a packaging material for packaging the oral composition. The weight ratio of the sugar alcohol to the cool fragrance is 10-1000.

4 Claims, 1 Drawing Sheet

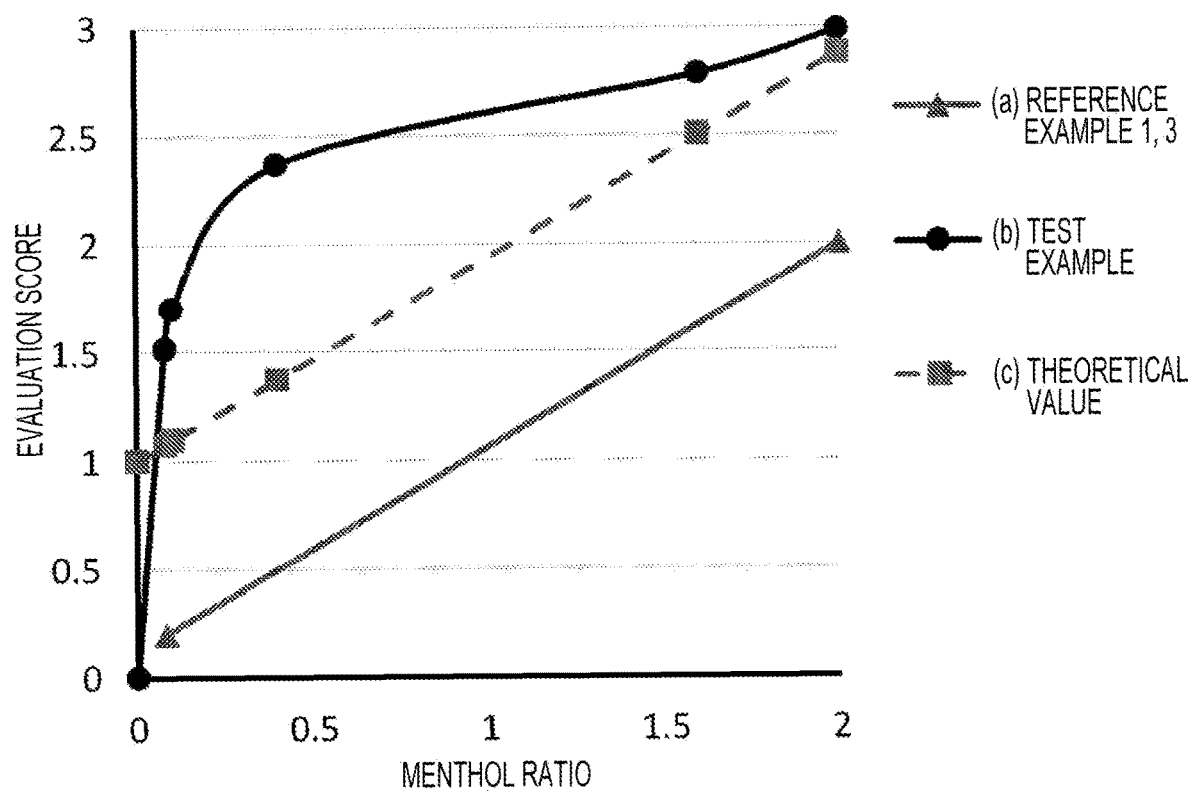

ORAL POUCH PRODUCT

CROSS REFERENCE TO RELATED APPLICATIONS

This application is a Continuation of PCT International Application No. PCT/JP2022/015843, filed on Mar. 30, 2022, which claims priority under 35 U.S.C. 119(a) to Patent Application No. 2021-058556, filed in Japan on Mar. 30, 2021, all of which are hereby expressly incorporated by reference into the present application.

TECHNICAL FIELD

The present invention relates to an oral pouch product.

BACKGROUND ART

In tobacco products such as cigarettes, inhaling flavor components volatilized by heating shredded tobacco or the like are delivered to users. When oral pouch products are inserted into the oral cavities of users, components such as nicotine in compositions leach out, thereby delivering flavor components or the like to users.

Patent Document 1 discloses a smokeless tobacco pastille containing a tobacco material, a natural gum binder, and a sugar alcohol. Patent Document 2 discloses a method for producing an oral pouched snuff product.

CITATION LIST

Patent Document

Patent Document 1: Japanese Unexamined Patent Application Publication (Translation of PCT Application) No. 2016-536982
Patent Document 2: Japanese Unexamined Patent Application Publication (Translation of PCT Application) No. 2019-507061

SUMMARY OF INVENTION

Technical Problem

It is an object of the present invention to provide an oral pouch product containing an oral composition capable of imparting a cooling sensation (also referred to as a "refreshing sensation, refreshing taste, or the like).

Solution to Problem

The inventors have conducted intensive studies and have found that the above object can be achieved by incorporating a sugar alcohol and a cooling agent into a nicotine-containing oral composition within a specific range, and have arrived at the present invention. The gist of the present invention is described below.

[1] An oral pouch product includes an oral composition containing nicotine, a sugar alcohol, and a cooling agent, and a packaging material that packages the oral composition,
  in which the ratio by weight of the sugar alcohol to the cooling agent in the oral composition is 10 or more and 1,000 or less.
[2] In the oral pouch product described in [1], the amount of the sugar alcohol contained in the oral composition is 15% by weight or more and 80% by weight or less.
[3] In the oral pouch product described in [1] or [2], the amount of the cooling agent contained in the oral composition is 0.08% by weight or more and 5.0% by weight or less.
[4] In the oral pouch product described in any one of [1] to [3], the sugar alcohol is one or more selected from the group consisting of xylitol, erythritol, sorbitol, mannitol, maltitol, and lactitol.
[5] In the oral pouch product described in any one of [1] to [4], the cooling agent is one or more selected from the group consisting of plants of the genus *Mentha* in the family Lamiaceae, extracts of plants of the genus *Mentha* in the family Lamiaceae, menthol, icilin, WS-12, WS-3, WS-5, and CPS-369.

Advantageous Effects of Invention

According to the present invention, it is possible to provide an oral pouch product containing an oral composition capable of imparting a cool feeling.

BRIEF DESCRIPTION OF DRAWINGS

FIG. 1 is a graph illustrating the relationship between the ratio by weight of menthol and the evaluation score of the cooling effect for (a) samples according to Reference examples 1 and 3, (b) samples according to Test examples 1 to 5, and (c) the theoretical values when the cooling effects of xylitol and menthol are assumed to be additive.

DESCRIPTION OF EMBODIMENTS

Although embodiments of the present invention will be described in detail below, these descriptions are examples (representative examples) of embodiments of the present invention, and the present invention is not limited to the contents of the descriptions as long as it does not depart from the spirit thereof.

In this specification, a numerical range expressed using "to" means a range including numerical values before and after "to" as lower and upper limit values, and "A to B" means A or more and B or less.

In an embodiment of the present invention, an oral pouch product contains an oral composition containing nicotine, a sugar alcohol, and a cooling agent, and a packaging material that packages the oral composition, in which the ratio by weight of the sugar alcohol to the cooling agent in the oral composition is 10 or more and 1,000 or less. When the oral composition contains the cooling agent and the sugar alcohol at the above-described ratio by weight, a cooler sensation can be imparted as compared with the case where only one of the cooling agent and the sugar alcohol is contained.

(Nicotine)

While the composition contains nicotine, the mode in which the composition contains nicotine is not particularly limited. For example, nicotine may be contained as a compound, or a nicotine-carrying substance such as a nicotine salt or stabilized nicotine (e.g., nicotine adsorbed on an ion-exchange resin) may be contained.

Examples of the nicotine-carrying substance include those in which nicotine is supported on ion-exchange resins as described above.

When nicotine is supported on an ion-exchange resin, the ion-exchange resin is used as a support. Examples of the ion-exchange resin can include weakly acidic cation-exchange resins. As the ion-exchange resin on which nicotine is supported, an ion-exchange resin containing, for example, 10% by weight to 20% by weight nicotine, which is called nicotine polacrilex, can be used. The ion-exchange resin used in nicotine polacrilex is a weakly acidic cation-exchange resin.

In the case of using nicotine polacrilex, nicotine is released from the resin composite through an ion-exchange process with cations originating from the oral composition dissolved in saliva upon use of the oral composition. Thereby, free nicotine is released from the water-insoluble resin composite and readily absorbed through the oral mucosa of a user.

When nicotine polacrilex is used, the amount of nicotine polacrilex added to the oral composition is usually 0.5% by weight or more, preferably 1.0% by weight or more, more preferably 2.0% by weight or more, based on the oral composition. From the viewpoint of the flavor of the oral composition, the amount of nicotine polacrilex added to the oral composition is usually 20.0% or less by weight, preferably 15.0% by weight or less, more preferably 10.0% by weight or less.

Tobacco leaves may be added as a nicotine source, or a nicotine-containing extract obtained by extracting a nicotine-containing substance such as tobacco leaves may be contained. The mode in which nicotine is incorporated is also not particularly limited. The above compound, nicotine source, or extract may be supported on a carrier or may be incorporated into the composition separately from the carrier. Among these modes, the addition of a nicotine-containing compound is preferred from the viewpoint of accurate supply of nicotine and ease of handling. When tobacco leaves are added, the composition and the pouch product usually tend to assume the color of the tobacco leaves. When a colorless nicotine-containing compound is used, a white composition and a white pouch product can be provided. This mode is advantageous for users who prefer white pouch products.

With regard to the modes described above, one mode may be used alone, or two or more modes may be used in combination.

The nicotine content of the composition is usually, but not particularly limited to, 0.1% by weight or more, and usually 6.7% by weight or less, from the viewpoint of user preference. When nicotine is present as an ion, the nicotine content is the nicotine ion content.

The nicotine content of the composition can be measured with a gas chromatography-mass spectrometer (GC-MS).

(Sugar Alcohol)

The sugar alcohol is obtained by reducing aldose or ketose. The sugar alcohol used in the present invention is a component typically used in oral products, and preferably has a negative heat of solution, i.e., undergoes an endothermic reaction when dissolved in water. Specifically, xylitol, erythritol, sorbitol, mannitol, maltitol, and lactitol are exemplified. Xylitol and erythritol are more preferred. Xylitol is particularly preferred.

The sugar alcohol content of the oral composition is usually, but not particularly limited to, 15% by weight or more, preferably 20% by weight or more, more preferably 30% by weight or more. The sugar alcohol content is usually 80% by weight or less, preferably 74% by weight or less, more preferably 60% by weight or less, particularly preferably 50% by weight or less. When the oral composition contains the sugar alcohol in an amount equal to or greater than the lower limit, a sufficient cooling sensation is easily obtained. The foregoing range of the sugar alcohol content may be the range of the amount when one of the examples described above is used alone, or may be the range of the total amount when two or more thereof are used in combination.

(Cooling Agent)

The cooling agent is a flavor that directly acts on sensory nerves responsible for cold sensation to give a cooling sensation, and more specifically, includes a compound that can act as an agonist of TRPM8 expressed in the sensory nerves. Examples of the cooling agent include plants of the genus *Mentha* in the family Lamiaceae, extracts of plants of the genus *Mentha* in the family Lamiaceae, menthol (also called menthol), icilin, WS-12, WS-3, WS-5, and CPS-369. Plants of the genus *Mentha* in the family Lamiaceae, extracts of plants of the genus *Mentha* in the family Lamiaceae, and menthol are preferred because they are widely used in oral compositions. All of WS-12, WS-3, WS-5, and CPS-369 are product names of compounds known as agonists of the channel receptor TRPM8.

Examples of the plants of the genus *Mentha* in the family Lamiaceae include peppermint, apple mint, water mint, Corsican mint, pennyroyal, hart's pennyroyal, Japanese mint, spearmint, horse mint, curly mint, ginger mint, and fragrant wintergreen. Examples of the extracts of the plants of the genus *Mentha* in the family Lamiaceae include mint oil obtained by a known method from the above-described species of the plants of the genus *Mentha* in the family Lamiaceae.

The cooling agent content of the oral composition is usually, but not particularly limited to, 0.08% by weight or more, preferably 1.0% by weight or more, more preferably 2.0% by weight or more. The cooling agent content is usually 5.0% by weight or less, preferably 4.0% by weight or less, more preferably 3.0% by weight or less. The foregoing range of the cooling agent content may be the range of the amount when one of the examples described above is used alone, or may be the range of the total amount when two or more thereof are used in combination.

In the present embodiment, the ratio by weight of the sugar alcohol to the cooling agent is usually 10 or more, preferably 25 or more. The ratio by weight is usually 1,000 or less, preferably 625 or less, more preferably 125 or less. When the ratio is within the above range, a cooler sensation can be obtained during use.

The composition of the present embodiment contains the sugar alcohol and the cooling agent in the above-described ranges, so that a more cooling sensation can be provided during use. The inventors speculate that the reason for this is as follows.

Cold stimuli to human skin are thought to be received by the channel-type receptor TPRM8, which is expressed on sensory nerves (Makoto Tominaga, Science of kampo medicine, Vol. 37, No. 3, 164-175, 2013). It is known that TPRM8 is usually activated at about 26° C. or lower and also activated by a ligand such as menthol and that the activation temperature threshold thereof is increased in the presence of menthol. That is, it is considered that the cooling sensation can be further obtained by simultaneously imparting menthol and heat absorption by the sugar alcohol.

When the composition of the present embodiment is inserted into the mouth of a user, the sugar alcohol is dissolved in water contained in saliva of the user to cause an endothermic reaction, and the temperature in the mouth is lowered to provide the user with a cooling sensation. In addition, the cooling agent, such as menthol, contained in the composition gradually leaches out and acts on TPRM8, thereby providing a cooling sensation and increasing the activation temperature threshold. According to this, the cooling effect of the sugar alcohol is synergistically intensified, and a cooler sensation is obtained.

(Other Substances)

The composition of the present embodiment may contain substances (also referred to as "other substances") other than nicotine, the sugar alcohol, or the cooling agent. Examples of the other substances include water, a flavor, a pH adjuster, a sweetener, a humectant, a bitterness inhibitor, a whitener, and an emulsifier. Other substances may be contained in a carrier, or may be contained in the composition separately from the carrier.

The amount of other substances contained in the composition is not particularly limited, and their formulation can be appropriately adjusted according to the product design.

The carrier is not particularly limited as long as it can support a substance. Examples thereof include solids and gels. In this specification, the term "gel" refers to a substance in which a sol-like decomposition product having fluidity is solidified and loses spontaneous fluidity while maintaining elasticity.

Examples of the type of carrier include, but are not particularly limited to, activated carbon, silica, starch, cellulose, other polysaccharides, and ion-exchange resins. Examples of the cellulose include microcrystalline cellulose (MCC), spherical cellulose, and porous cellulose. These substances can be appropriately selected from the viewpoint of flexibility in adjusting the bulk density of the composition. One of the substances may be used alone, or any two or more of them may be used in combination in any type and ratio.

The carrier content of the composition is usually, but not particularly limited to, 10% by weight or more, preferably 20% by weight or more, more preferably 30% by weight or more, from the viewpoint of improvement in quality, i.e., the inhibition of effusion of water during production or storage of the product, and from the viewpoint of imparting an appearance desirable for users by increasing the whiteness of the product. The upper limit thereof need not be particularly limited, but is usually 55% by weight or less, preferably 45% by weight or less, more preferably 35% by weight or less, from the viewpoint of the limits of other raw materials that can be blended therewith.

The water content (moisture content) of the composition of the present embodiment is usually, but not particularly limited to, 5% by weight or more, preferably 6% by weight or more, more preferably 7% by weight or more. The content is usually 15% by weight or less, preferably 10% by weight or less. The moisture content can be adjusted by adjusting the amount of water to be added or by providing heat treatment or drying treatment in the production stage.

The water content (moisture content) of the composition is measured with a heat-drying moisture analyzer (for example, HB43-S, available from METTLER TOLEDO). In the measurement, a sample is placed in a predetermined container and heated in such a manner that the temperature reaches 100° C. The measurement is terminated when the amount of change becomes 1 mg or less for 60 seconds. The moisture content is calculated from the weighed values before and after the heating.

The method for measuring the moisture content in this specification is similarly used to the measurement of the moisture content of an object other than the composition, for example, a mixture in a method for producing a composition described below.

The type of the flavor included in the other substances is not particularly limited, and flavors other than the cooling agent are included. Examples thereof include leaf tobacco extract, natural vegetable flavors (such as cinnamon, sage, herb, chamomile, kudzu, sweet *Hydrangea* leaves, clove, lavender, cardamom, nutmeg, bergamot, geranium, honey essence, rose oil, lemon, orange, cassia bark, caraway, jasmine, ginger, coriander, vanilla extract, cassia, coffee, celery, cascarilla, sandalwood, cocoa, ylang-ylang, fennel, anise, licorice, Saint John's bread, plum extract, and peach extract), saccharides (such as glucose, fructose, isomerized sugar, caramel, honey, and molasses), cocoas (such as powder and extract), esters (such as isoamyl acetate, linalyl acetate, isoamyl propionate, and linalyl butyrate), ketones (such as menthone, ionone, damascenones, and ethyl maltol), alcohols (such as geraniol, linalool, anethole, and eugenol), aldehydes (such as vanillin, benzaldehyde, and anisaldehyde), lactones (such as γ-undecalactone and γ-nonalactone), animal flavors (e.g., musk, ambergris, civet, and castoreum), and hydrocarbons (such as limonene and pinene). One of these substances may be used alone, or any two or more of them may be used in combination in any ratio.

Examples of the type of the pH adjuster include, but are not particularly limited to, sodium carbonate, sodium hydrogen carbonate, potassium carbonate, potassium hydrogen carbonate, anhydrous sodium phosphate, sodium dihydrogen phosphate, trisodium phosphate, and sodium citrate. From the viewpoint of the influence on the taste of the product, sodium carbonate, potassium carbonate, and sodium dihydrogen phosphate are preferred. One of these substances may be used alone, or any two or more of them may be used in combination in any ratio.

The sugar alcohol contained in the composition of the present embodiment is commonly used as a sweetener. The composition may contain other sweeteners in addition to the sugar alcohol described above. Examples the types of the other sweeteners include, but are not particularly limited to, acesulfame potassium, sucralose, and aspartame. One of these substances may be used alone, or any two or more of them may be used in combination in any ratio.

An example of the bitterness inhibitor is, but not particularly limited to, soybean lecithin. Soybean lecithin is a phospholipid. Examples thereof include phosphatidylcholine, phosphatidylethanolamine, and phosphatidic acid. One of these substances may be used alone, or any two or more of them may be used in combination in any ratio.

Examples of the type of the humectant include, but are not particularly limited to, glycerine and propylene glycol. From the viewpoint of product storage stability, glycerine is preferred. One of these substances may be used alone, or any two or more of them may be used in combination in any ratio.

Examples of the type of the whitener include, but are not particularly limited to, silicon dioxide, titanium dioxide, and calcium carbonate. From the viewpoint of the influence on the taste of the product, silicon dioxide is preferred. One of these substances may be used alone, or any two or more of them may be used in combination in any ratio.

Examples of the type of the emulsifier include, but are not particularly limited to, emulsifiers added to foods. The emulsifier can be, for example, at least one selected from the group consisting of sucrose fatty acid esters, organic and fatty acid esters of glycerine, polyglycerine esters of fatty acid, and lecithin. Examples of the sucrose fatty acid esters include sucrose palmitate and sucrose stearate. Examples of the organic and fatty acid esters of glycerine include succinic and fatty acid esters of glycerine and diacetyl tartaric and fatty acid esters of glycerine. Examples of polyglycerine esters of fatty acid include diglycerine esters of fatty acid, triglycerine esters of fatty acid, and decaglycerine esters of fatty acid. One of these substances may be used alone, or any two or more of them may be used in combination in any ratio.

The amount of each of the components described above (excluding the moisture content) can also be calculated from the amount of raw material fed.

(pH of Composition)

The pH of the composition at a measurement temperature of 22° C. is not particularly limited, but is usually 6.0 or more, preferably 7.0 or more, more preferably 8.0 or more, and usually 10.0 or less, preferably 9.0 or less, from the viewpoint of the influence on the taste of the product. The pH can be adjusted by controlling the amount of pH adjuster added. Not only the above pH values but also the pH values in this specification are values measured at a measurement temperature of 22° C.

The pH of the composition at a measurement temperature of 22° C. is measured with a pH analyzer (such as LAQUA F-72 flat ISFET pH electrode, available from Horiba, Ltd.) by adding 20 ml of water to 2 g of the composition, shaking the mixture for 10 minutes, and measuring the pH of the supernatant.

The instrument is calibrated by three-point calibration, for example, with a phthalate pH standard solution (pH: 4.01), a neutral phosphate pH standard solution (pH: 6.86), and a borate pH standard solution (pH: 9.18) (all available from Wako Pure Chemical Industries, Ltd.).

(Packaging Material)

The packaging material (pouch) is not particularly limited as long as it can package the above-described composition, is not dissolved in water, and is permeable to a liquid (such as water and saliva) and a water-soluble component in the composition, and a known packaging material can be used. Examples of the material of the packaging material include cellulose-based nonwoven fabrics. A commercially available nonwoven fabric may be used. A pouch product can be produced by forming a sheet composed of such a material into a bag shape, introducing the composition into the bag, and sealing the bag by means of, for example, heat sealing.

The basis weight of the sheet is usually, but not particularly limited to, 12 gsm or more and 54 gsm or less, preferably 24 gsm or more and 30 gsm or less.

The thickness of the sheet is usually, but not particularly limited to, 100 μm or more and 300 μm or less, preferably 175 μm or more and 215 μm or less.

A water-repellent material may be partially applied to at least one of the inner surface and the outer surface of the packaging material. As the water-repellent material, a water-repellent fluorocarbon resin is suitable. A specific example of such a water-repellent fluorocarbon resin is AsahiGuard (registered trademark) available from AGC Inc. The water-repellent fluorocarbon resin is applied, for example, to packaging materials for foods and products containing fats and oils, such as confectionery, dairy products, daily dishes, fast foods, and pet foods. Thus, such a water-repellent fluorocarbon resin is safe even when applied to a pouch to be placed in the oral cavity. The water-repellent material need not be a fluorocarbon resin and may be any material having a water-repellent effect, such as a paraffin resin, a silicon resin, or an epoxy resin.

The packaging material may contain any component. Examples thereof include raw materials for controlling aroma and tastes, flavors, additives, tobacco extracts, and pigments. These components may be incorporated in any manner. For example, the components may be applied to or infiltrated into the surface of the packaging material, or when the packaging material is composed of fibers, the components may be incorporated into the fibers.

The appearance of the packaging material is not particularly limited. The appearance may be not only non-transparent but also translucent or transparent. In this case, the composition packaged in the packaging material can be seen through.

[Pouch Product]

The pouch product is not particularly limited as long as it has the above-described composition and the above-described packaging material for packaging the composition (i.e., the above-described composition is enclosed in the above-described packaging material).

The size and weight of the pouch product are not particularly limited. With regard to the size of the pouch product before use, the long side may be 25 mm or more, 28 mm or more, 35 mm or more, or 38 mm or more, and 40 mm or less, or 38 mm or less. The short side may be 10 mm or more and 20 mm or less, or 14 mm or more and 18 mm or less. The weight of the pouch product before use may be 0.1 g or more and 2.0 g or less, or 0.3 g or more and 1.0 g or less.

The proportion of the weight of the composition to the total weight of the pouch product is usually, but not particularly limited to, 80% by weight or more, preferably 85% by weight or more, more preferably 90% by weight or more, and usually 99% by weight or less, preferably 97% by weight or less, more preferably 95% by weight or less.

(Method for Producing Pouch Product)

The method for producing the pouch product is not particularly limited, and a known method can be used. An example of a known method that can be used is a method in which the composition is placed in a bag-shaped nonwoven fabric and then the nonwoven fabric is sealed.

The composition is placed in the packaging material, and then the packaging material is sealed. Thereafter, additional water may be added to provide the composition with the desired moisture content. For example, in the case where the amount of water contained in the target composition is 15% by weight and where the amount of water contained in the composition prepared in the foregoing composition preparation process is 5% by weight, the remaining 10% by weight of water is added.

<Application of Pouch Product>

Examples of applications (modes of use) of the pouch product include, but are not particularly limited to, oral tobaccos, such as chewing tobacco, snuff, and compressed tobacco, and nicotine-containing preparations called nicotine pouches. These are inserted between the lips and gums in the oral cavity to enjoy their taste and flavor.

EXAMPLES

The present invention will be described more specifically by way of examples, but the present invention is not limited to the description of the following examples without departing from the gist of the present invention.

<Preparation of Sample>

Microcrystalline cellulose (MCC), xylitol (Xyl), and menthol (Menthol) were mixed in ratios by weight given in Table 1 to prepare compositions each having a total weight of 0.4 g. Samples of Reference examples 1 to 3 and Test examples 1 to 5 were produced by placing the compositions into bag-shaped nonwoven fabrics and then sealing the nonwoven fabrics.

TABLE 1

| | Ratio by weight | | | Estimated score |
| --- | --- | --- | --- | --- |
| | MCC | Xyl | Menthol | |
| Reference example 1 | 4 | — | 0.008 | 0.2 |
| Reference example 2 | 4 | 5 | 0 | 1 |
| Reference example 3 | 4 | — | 0.2 | 2 |
| Test example 1 | 4 | 5 | 0.008 | — |
| Test example 2 | 4 | 5 | 0.01 | — |
| Test example 3 | 4 | 5 | 0.04 | — |
| Test example 4 | 4 | 5 | 0.16 | — |
| Test example 5 | 4 | 5 | 0.2 | — |

<Sensory Evaluation>

Each sample was evaluated in the following manner.

A predetermined amount of water (Reference example: 0.5 mL, Test example: 1 mL) was dropped under the tongue of each panelist with a dropper. Then each sample was further inserted under the tongue.

The cooling effect immediately after insertion of the sample was marked at a corresponding position on a straight line representing 0 to 3 points. Thereafter, the marked position was measured to calculate an evaluation score in one decimal place.

To standardize the evaluation criteria among the panelists, each of the panelists evaluated the control samples (Reference examples 1 to 3) before the test examples, and checked how many points (estimated scores given in Table 1) the cooling sensation felt in each control sample corresponded to in this sensory evaluation.

In addition, for each evaluation of each sample, an interval was provided until the cooling sensation derived from menthol or the like disappeared (1 to 2 minutes), and then the next sample was evaluated.

After Reference examples 1 to 3 were sequentially evaluated, the samples of the respective test examples were sequentially evaluated.

Table 2 presents the evaluation scores of the panelists A to F, the mean scores thereof, and the standard deviations, in the test examples. FIG. 1 illustrates the relationship between the mean values of the evaluation scores of the panelists and the amounts of menthol in (a) Reference examples 1 and 3 and (b) Test examples 1 to 5. The score of the cooling sensation determined when the cooling effects of xylitol and menthol are assumed to be additive was calculated as a theoretical value by calculating the slope of the straight line passing through Reference examples 1 and 3 and adding 1, which is the evaluation score of Reference example 2, and presented as a straight line (c).

TABLE 2

| | A | B | C | D | E | F | Mean value | Standard deviation |
| --- | --- | --- | --- | --- | --- | --- | --- | --- |
| Test example 1 | 1.3 | 1.0 | 1.7 | 1.8 | 2.5 | 0.8 | 1.51667 | 0.61779 |
| Test example 2 | 1.8 | 1.4 | 1.9 | 1.0 | 2.6 | 1.5 | 1.7 | 0.54406 |
| Test example 3 | 2.4 | 2.1 | 2.2 | 2.2 | 3.0 | 2.3 | 2.36667 | 0.3266 |
| Test example 4 | 2.8 | 3.0 | 2.8 | 2.5 | 2.8 | 2.8 | 2.78333 | 0.16021 |
| Test example 5 | 3.0 | 3.0 | 3.0 | 3.0 | 2.9 | 3.0 | 2.98333 | 0.04082 |

FIG. 1 clearly indicated that Test examples 1 to 5 exhibited higher evaluation scores than the straight line (c). That is, the results suggested that the cooling effect was synergistically intensified when the sugar alcohol and the cooling agent are contained in the oral composition.

What is claimed is:

1. An oral pouch product comprising an oral composition containing nicotine, a sugar alcohol, and a cooling agent, and a packaging material that packages the oral composition,
   wherein the oral pouch product has a cooler sensation resulting from a cooling effect which is synergistically intensified by an addition of the sugar alcohol and the cooling agent than that resulting from a cooling effect calculated by assuming cooling effects of the cooling agent and the sugar alcohol are additive,
   wherein a ratio by weight of the sugar alcohol to the cooling agent in the oral composition is 10 or more and 1,000 or less,
   wherein the sugar alcohol is one or more selected from the group consisting of xylitol, erythritol, sorbitol, mannitol, maltitol, and lactitol,
   wherein an amount of the sugar alcohol contained in the oral composition is 20% by weight or more and 80% by weight or less, and
   wherein the cooling agent is one or more selected from the group consisting of plants of genus *Mentha* in family Lamiaceae, extracts of plants of the genus *Mentha* in the family Lamiaceae, menthol, icilin, WS-12, WS-3, WS-5, and CPS-369.

2. The oral pouch product according to claim 1, wherein an amount of the cooling agent contained in the oral composition is 0.08% by weight or more and 5.0% by weight or less.

3. A method for intensifying a cooling effect of an oral pouch product which comprises an oral composition and a packaging material that packages the oral composition, including
   a step of adding a sugar alcohol and a cooling agent to the oral composition so that a ratio by weight of the sugar alcohol to the cooling agent in the oral composition is 10 or more and 1,000 or less and so that an amount of the sugar alcohol contained in the oral composition is 20% by weight or more and 80% by weight or less,
   wherein the sugar alcohol is one or more selected from the group consisting of xylitol, erythritol, sorbitol, mannitol, maltitol, and lactitol,
   wherein the cooling agent is one or more selected from the group consisting of plants of genus *Mentha* in family Lamiaceae, extracts of plants of the genus *Mentha* in the family Lamiaceae, menthol, icilin, WS-12, WS-3, WS-5, and CPS-369, and
   wherein the oral pouch product has a cooler sensation resulting from a cooling effect which is synergistically intensified by an addition of the sugar alcohol and the cooling agent than that resulting from a cooling effect calculated by assuming cooling effects of the cooling agent and the sugar alcohol are additive.

4. The method according to claim 3, wherein in the step of adding, the cooling agent is added so that an amount of the cooling agent contained in the oral composition is 0.08% by weight or more and 5.0% by weight or less.

* * * * *